US007113820B2

(12) United States Patent
Schlegel et al.

(10) Patent No.: US 7,113,820 B2
(45) Date of Patent: Sep. 26, 2006

(54) REAL-TIME, HIGH FREQUENCY QRS ELECTROCARDIOGRAPH

(75) Inventors: Todd T. Schlegel, Nassau Bay, TX (US); Jude L. DePalma, Pueblo, CO (US); Saeed Moradi, Houston, TX (US)

(73) Assignee: The United States of America as represented by the Administration of the National Aeronautics and Space Administration, Washington, DC (US)

( * ) Notice: Subject to any disclaimer, the term of this patent is extended or adjusted under 35 U.S.C. 154(b) by 660 days.

(21) Appl. No.: 09/906,013

(22) Filed: Jul. 12, 2001

(65) Prior Publication Data

US 2003/0013978 A1 Jan. 16, 2003

(51) Int. Cl.
*A61B 5/0472* (2006.01)

(52) U.S. Cl. ........................................ 600/523; 600/509
(58) Field of Classification Search ................. 600/521, 600/509, 523, 515
See application file for complete search history.

(56) References Cited

U.S. PATENT DOCUMENTS

| 4,422,459 | A | 12/1983 | Simson | 128/702 |
| 5,046,504 | A | 9/1991 | Albert et al. | 128/696 |
| 5,117,833 | A | 6/1992 | Albert et al. | 128/702 |
| 5,348,020 | A | 9/1994 | Hutson | 128/696 |
| 5,655,540 | A | 8/1997 | Seegobin | 128/702 |
| 5,819,741 | A | * 10/1998 | Karlsson et al. | 600/523 |
| 5,954,664 | A | 9/1999 | Seegobin | 600/515 |
| 6,058,328 | A | * 5/2000 | Levine et al. | 607/14 |
| 2003/0208129 | A1 | 11/2003 | Beker et al. | |

FOREIGN PATENT DOCUMENTS

WO    WO 01/49160    7/2001

OTHER PUBLICATIONS

Shimon Abboud, Progress in Cardiovascular Diseases, Mar./Apr. 1993, vol. XXXV, No. 5, pp. 311–328.
R. Lewis Gable & Brian Dengler, Arrhythmia Research Technollogy v. Corazonix Corp.

* cited by examiner

*Primary Examiner*—Kennedy Schaetzle
(74) *Attorney, Agent, or Firm*—Theodore U. Ro

(57) ABSTRACT

Real time cardiac electrical data are received from a patient, manipulated to determine various useful aspects of the ECG signal, and displayed in real time in a useful form on a computer screen or monitor. The monitor displays the high frequency data from the QRS complex in units of microvolts, juxtaposed with a display of conventional ECG data in units of millivolts or microvolts. The high frequency data are analyzed for their root mean square (RMS) voltage values and the discrete RMS values and related parameters are displayed in real time. The high frequency data from the QRS complex are analyzed with imbedded algorithms to determine the presence or absence of reduced amplitude zones, referred to herein as "RAZs". RAZs are displayed as "go, no-go" signals on the computer monitor. The RMS and related values of the high frequency components are displayed as time varying signals, and the presence or absence of RAZs may be similarly displayed over time.

34 Claims, 16 Drawing Sheets

REAL-TIME, HIGH FREQUENCY QRS ELECTROCARDIOGRAPH

The invention described herein was made by employees of the United States Government and may be manufactured and used by or for the government for government purposes without payment of any royalties thereon or therefore.

FIELD OF THE INVENTION

The present invention relates generally to the field of electrocardiography, and more particularly to a real-time processing system and method to analyze and display electrocardiographic signals.

BACKGROUND OF THE INVENTION

Diagnosis of abnormal cardiac conditions has relied in the past on visible alterations in the P, QRS, and T-waves, i.e. portions of the electrocardiograph periodic signal. The electrocardiograph signal includes a low frequency portion and an impressed or imbedded high frequency portion, and it has been found that although the higher frequency portion of the signal is not particularly visible, it contains information that provides greater sensitivity in determining certain abnormalities, notably myocardial ischemia and infarction.

The conventional electrocardiogram (ECG) can be a very insensitive diagnostic tool. For example, a significant percentage of individuals presenting to a hospital emergency room with an actual myocardial infarction (heart attack) will have a normal 12-lead conventional ECG. In addition, the conventional ECG accurately reflects only the predominant low-frequency electrical activity of the heart. It tells the clinician little or nothing about the less predominant high frequency components of the heart's electrical signal embedded within the various lower-frequency waves of the conventional ECG.

From off-line studies, it is known that a diminution of the higher frequency components within the central portion of the QRS complex of the ECG can be a highly sensitive indicator for the presence of myocardial ischemia or infarction, more sensitive, for example, than changes in the ST segment of the conventional low-frequency electrocardiogram. However, until now, there has been no device capable of displaying, in real time, changes in these high frequency QRS components in the monitored patient. While academic software programs have been designed that analyze the central high frequency QRS components, all such programs involve laborious off-line calculations and post-processing, and therefore have little if any clinical utility, being strictly research tools. Thus, there remains a need for a system and method that analyzes high frequency components over the entire QRS interval in real time for usefulness in the clinical environment. Such a system should perform, in real time, all of the complex digital sampling, averaging, and filtering that is required to generate high frequency QRS ECG signals. The system should also thereafter update these high frequency QRS ECG signals, as well as other derived parameters, in real time on a beat-to-beat basis, supplementing the diagnostic information being obtained from the conventional (i.e. low frequency) ECG complexes at the same time.

The higher frequency signals in the central portion of the QRS ECG complex that have generated the most research interest in terms of off-line detection of ischemia and infarction are those signals in the range of 150 to 250 Hz. The raw, analog ECG signal is typically sampled at $\geq 500$ samples per second (to digitize the signal) in order to adequately satisfy the Nyquist rate of sampling at least twice the highest frequency of interest and in order to retain the information in the signal without loss. In the past, the sampled data have been stored, and then later processed to provide potentially useful information to the researcher.

On the other hand, Simpson, in U.S. Pat. No. 4,422,459, teaches a system which analyzes only the late portion of the QRS interval and early portion of the ST segment, and in an off-line fashion (i.e. from previously stored data) to indicate cardiac abnormalities, in particular the propensity for cardiac arrhythmia. The late portion of a post myocardial infarct patient's QRS waveform contains a high frequency (40–250 Hz) signal tail which is indicative of a tendency toward ventricular tachycardia. The system in Simpson digitally processes and filters a patient's QRS signals in a reverse time manner to isolate the high frequency tail and avoid the filter ringing which would otherwise hide the signal. Thus, in order to do so, Simpson presupposes that the data are stored so that they can be processed in reverse time order.

Albert et al., U.S. Pat. No. 5,117,833, partially focuses on analyzing signals within the mid-portion of the QRS interval for the indication of cardiac abnormality. The system of Albert et al. uses a known technique of building up data points to derive an average of heartbeat characteristics in order to enhance signal to noise ratio. Data are collected and filtered and then stored for subsequent analysis. Thus, the system does not teach a cardiac monitor which provides the data analysis immediately from the data derived from a patient, i.e. in "real-time".

Albert et al., U.S. Pat. No. 5,046,504, similarly teaches the acquisition of QRS data and subsequent analysis. Routine calculations are performed from the data previously calculated and stored. Further, this system teaches producing a set of digital spectrum values representative of an approximate power density spectrum at each of a large number of generally equally spaced sampling time intervals of the ECG waveform.

Seegobin, in U.S. Pat. Nos. 5,655,540 and 5,954,664, provides a method for identifying coronary artery disease. The method relies on a database of high and low frequency ECG data taken from known healthy and diseased subjects. Comparison of the data has led to a "Score" component, indicating deviation of a patient's data from the norm. This reference is rather calculation intensive, and does not suggest monitoring the condition of a patient, but rather is utilized as an off-line diagnostic tool.

Hutson, U.S. Pat. No. 5,348,020, teaches a technique of near real-time analysis and display. The technique includes inputting ECG data from multiple, sequential time intervals and formatting those data into a two-dimensional matrix. The matrix is then decomposed to obtain corresponding singular values and vectors for data compression. The compressed form of the matrix is analyzed and filtered to identify and enhance ECG signal components of interest. As with other systems, this reference focuses on late potentials, a fraction of the QRS interval, as the tool to identify cardiac disease.

Finally, *High-Frequency Electrocardiogram Analysis of the Entire QRS in the Diagnosis and Assessment of Coronary Artery Disease* by Abboud (*Progress in Cardiovascular Diseases*, Vol. XXXV, No. 5 (March/April), 1993: pp 311–328) teaches the concept of "reduced amplitude zone" (RAZ) as a diagnostic tool. However, this reference also uses post-processing, and provides no teaching of a real-time analysis system.

Thus, there remains a need for an electrocardiograph that analyzes, in real time, the high frequency components of the QRS complex in order to provide an effective monitor for patients with specific cardiac function abnormalities. The present invention is directed to such an electrocardiograph.

SUMMARY OF THE INVENTION

The present invention addresses these and other needs in the art by providing a real time display of various aspects of the QRS complex. The invention also provides a system for such a display, and a method of displaying such aspects.

The present invention advances the state of the art by taking high frequency electrocardiographic data immediately as they are sensed from a patient, manipulating the data in conjunction with the conventional low frequency signals, and displaying the high frequency data in real time in a useful form on a computer screen or monitor. In one aspect, the invention displays the high frequency data from the QRS complex in microvolts adjacent to a display of the conventional ECG data in millivolts. In another aspect of the invention, the high frequency data are analyzed for their root mean square (RMS) voltage values (as well as for related values such as the high frequency energy (HFQE) and high frequency integral of absolute value (HFAV), both described hereinafter), with the discrete, lead-by-lead values being displayed in real time as useful diagnostic indicators for ischemia. Also, the high frequency data from the QRS complex are analyzed with imbedded algorithms to determine the presence or absence of reduced amplitude zones, referred to hereinafter as "RAZs". The given RAZ, of which there are at least three possible variations (i.e., the "Abboud" RAZ, the "NASA" RAZ, and the skewness-kurtosis or "S-K" RAZ, all described below), is displayed as a real-time "go, no-go" signal on the screen. Finally, in still another aspect of the invention, not only the presence or absence any one of the three variations of RAZs, but also the RMS and related values (HFQE and HFAV) are displayed against time as time varying signals.

In still another aspect of the invention, the electrocardiograph of this invention detects and aligns R-waves and QRS complexes and analyzes these ECG signals after digitization at high sampling rates of at least 500 samples per second, but preferably at sampling rates of 1000 samples per second or greater. The system also signal averages consecutive QRS electrocardiographic complexes in a user-adjustable fashion to increase the signal-to-noise ratio. The resulting averaged signal is filtered, using non-recursive digital bandpass filters with varying high and low frequency cutoffs, and displayed in real time along with several other derived numerical measures described herein including the power spectrum of the filtered data. The resulting displays provide a clinician with real-time information with respect to changes in the high frequency ECG complex that may be indicative of myocardial ischemia, myocardial infarction, or of changes in myocardial conduction that are unrelated to myocardial ischemia or infarction.

The invention includes a number of features that are neither shown nor suggested in the art, including a real-time display of cardiac electrical data that have been manipulated in such a way as to provide a clear indication of ischemia and infarction. The invention further includes a number of user selectable parameters to enhance the information provided to the clinician. Finally, the invention provides a number of displays, juxtaposed in real time, to provide a side-by-side comparison of various aspects of the QRS complex in real time.

These and other features of the invention will be apparent to those of skill in the art from a review of the following detailed description along with the accompanying drawings.

DETAILED DESCRIPTION OF A PREFERRED EMBODIMENT

Figure 1:
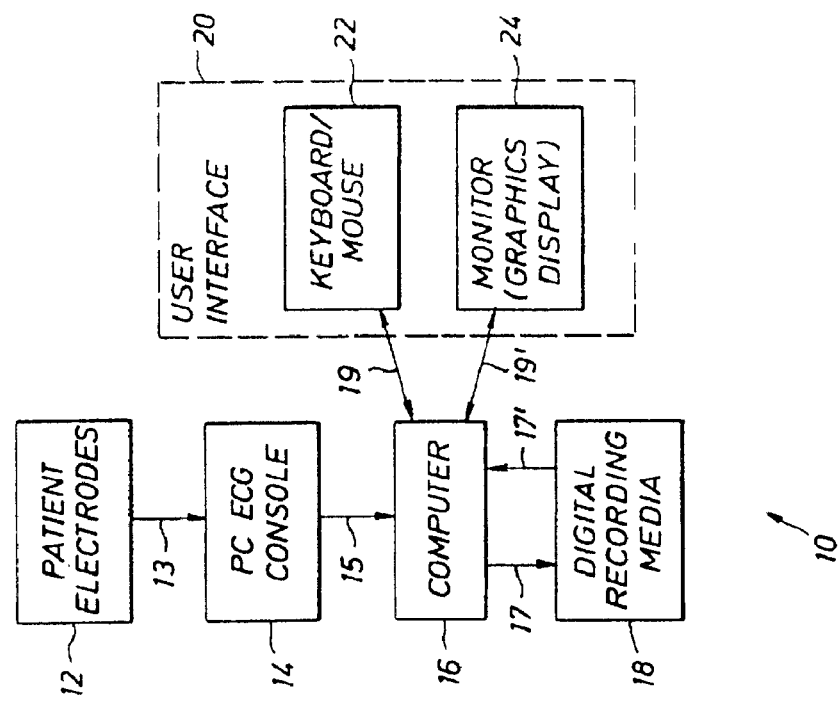
FIG. 1 is a schematic diagram of the overall system of this invention.

FIG. 1 shows a simplified, functional, block diagram of a real-time high frequency QRS electrocardiograph 10 constructed in accordance with the present invention. The invention monitors the cardiac function of a patient with a plurality of patient electrodes 12. The electrodes provide measurements of cardiac electrical function at various contact points on the skin of a patient in the conventional manner. For example, in the conventional 12-lead configuration, 10 electrodes placed upon the skin of the patient in the conventional configuration result in eight channels of incoming data. These eight channels are in turn translated into 12 leads of data on the patient monitor inasmuch as data for one of the bipolar limb leads and for all of the augmented unipolar limb leads can be derived if data for any two of the bipolar limb leads are already known. The analog measurements are coupled to a console 14 by way of a communications channel such as for example a cable 13. The console components are shown in greater detail in FIG. 2.

The console 14 conditions and digitizes the analog signal and provides the digitized signal to a computer 16 by way of a communications channel 15, which may preferably be a conventional cable or a communication channel by radio frequency wave. The structure and function of the computer is shown and described below in respect of FIG. 3. The computer 16 is programmed to display the ECG signal in real time, although the ECG signal may also be stored on a digital recording medium 18 over a communications channel 17 for later display over a communications channel 17'.

The computer 16 is coupled to a user interface 20 which preferably includes communications devices 22 such as a mouse, keyboard, and/or touch screen. The user interface further includes a monitor 24 for user controllable graphic display of the ECG and various aspects of the signal, a feature of the present invention. The computer 16 is coupled to the interface 20 by way of bidirectional communications channels 19 and 19', for example. The aspects of the graphical display are shown in greater detail and described below in respect of FIGS. 4 through 17.

Figure 2:
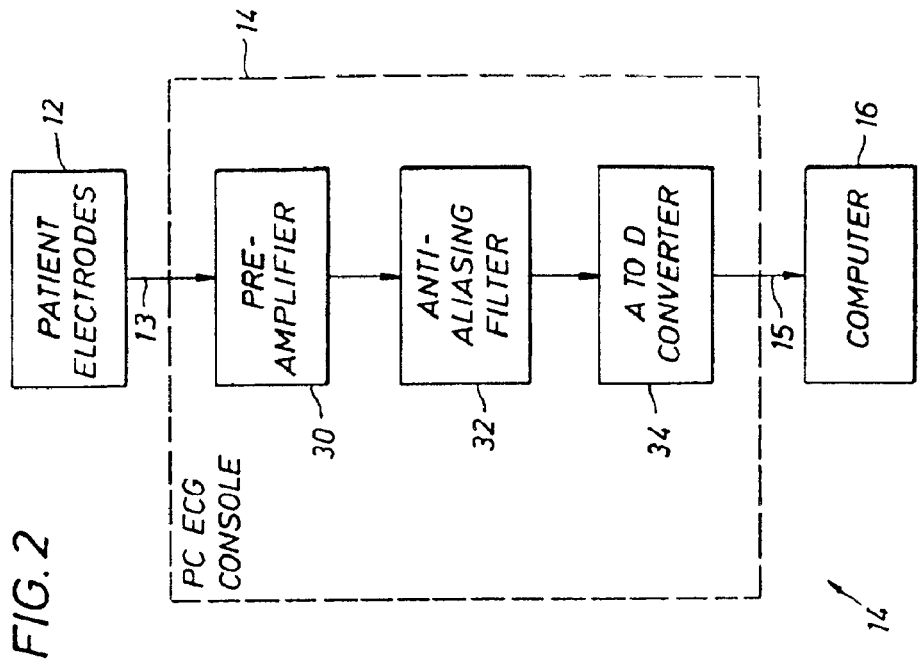
FIG. 2 is a schematic diagram of a detail of FIG. 1.

FIG. 2 depicts the structure of the console 14 in greater detail. As previously described, the patient is wired with a set of electrodes 12, such as for example a conventional set of ten electrodes for a 12-lead electrocardiograph to monitor cardiac function from different aspects of the patient's body. The electrodes 12 provide a set of analog electrical signals to the console 14, where they are received by a pre-amplifier 30 to boost the amplitude of the weak ECG signals. The amplified signals are then fed to an anti-aliasing filter 32. The filtered signals are then fed to an analog to digital converter 34, where the signals are digitized at least the Nyquist rate, preferably 1,000 Hz or greater, to retain all of the information contained in the analog signals. The sampled/digitized signals are then sent to the computer 16 by an appropriate medium 15.

Figure 3:
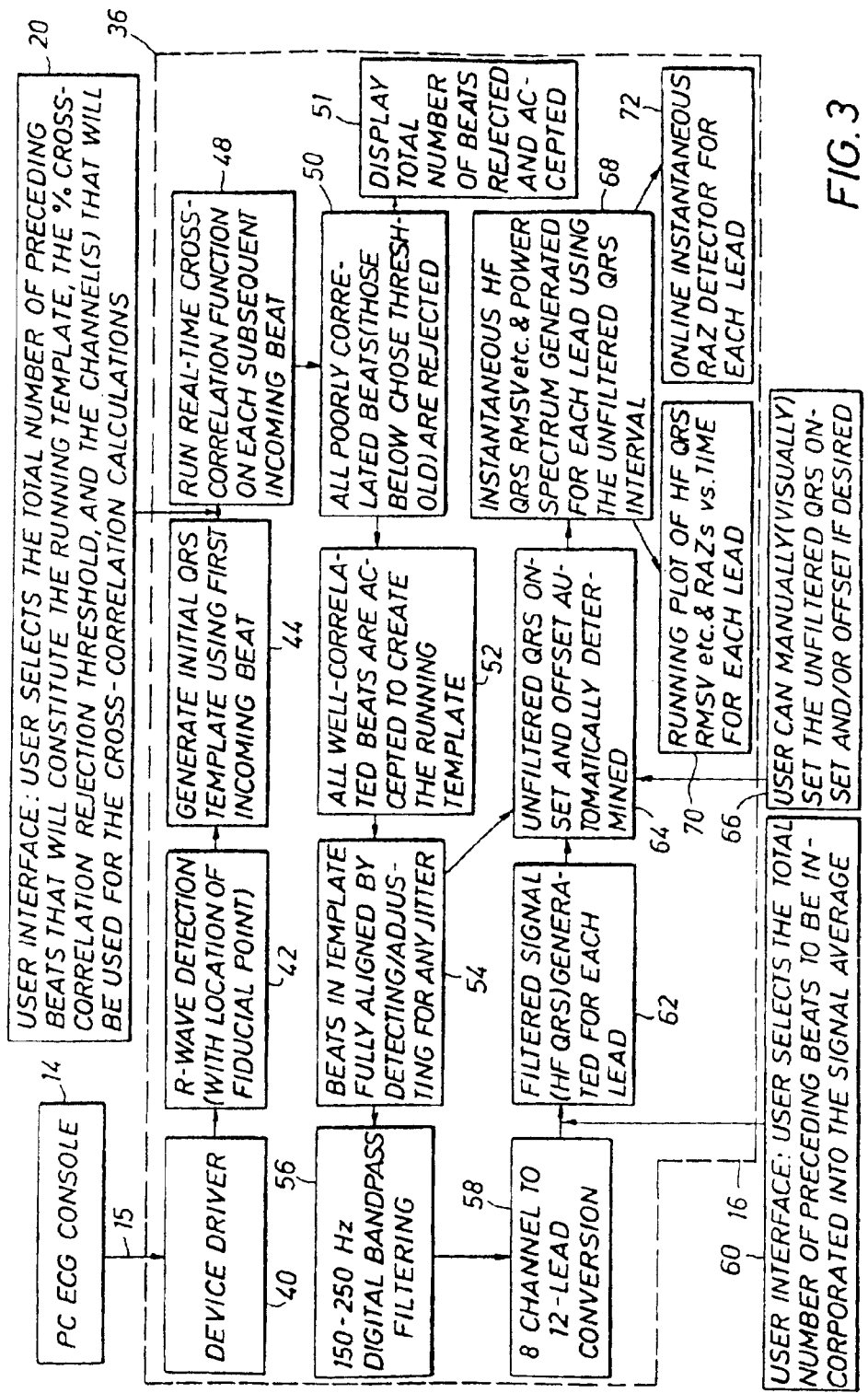
FIG. 3 is a schematic diagram of the logic carried out by the invention.

The operation of the computer 16 is depicted in FIG. 3. The console 14 feeds the digitized ECG signals to the computer via a communications channel 15, as previously described. The computer 16 also interfaces with the user interface 20. The computer 16 receives the ECG signals into a device driver 40, which is simply the interface device and program for the console and computer. The device driver 40 provides the ECG signals in parallel to an R-wave detection block 42 to synchronize the system for the start of each heartbeat by locating the fiducial point. The following requirements must be met for temporal averaging to work effectively. First, the signal of interest must be repetitive and relatively invariable. Time varying signals, such as ectopic or premature complexes, are eliminated before averaging by comparing incoming signals against a previously established template through the use of a real-time cross-correlating technique. Second, the signal of interest must be timelocked to a fiducial point, such as near the peak of the QRS complex, that is easily detectable and serves as a timing reference for the averaging algorithm. If the signal of interest does not have a fixed, temporal relationship with the timing reference point, the resultant averaged signal will be filtered and distorted due to reference jitter, with subsequent loss of the high frequency components. Third, the signal of interest and the noise must be independent and remain independent during averaging.

Once the fiducial point has been located for each incoming beat, the digitized signals are fed to block 44 where initial templates of the QRS complexes are generated. The present invention includes running signal averages of the QRS complexes that constitute templates, with the number of individual beats in the running templates being selectable by the user on the user interface 20. The user can also determine the percent of cross-correlation between each new incoming beat and the templates which will be detected as a departure from the norm, and which channel(s) that will be used for the cross-correlation functions.

With the user-selected inputs as just described, the system in block 48 runs a real-time cross-correlation function on each subsequent incoming beat. In block 50, those beats which are below the threshold set by the user (or set by the system default) are rejected, with block 52 accepting only well-correlated beats to create the running templates. This feature helps to eliminate noisy, unreliable waveforms when creating the running templates. From this block, the user interface displays a continuously updated running total of the number of beats accepted and rejected in block 51, a feature of the invention.

Block 54 then aligns the beats by detecting and adjusting for any signal jitter, which may be created by any number of well-known factors, including minor inconsistencies in the detection of the fiducial point, movement by the patient or even respiration by the patient. The aligned, jitter-corrected waveform is then fed to block 56, a band-pass filter, preferably 150–250 Hz, to select only the frequencies of interest in the waveform. Finally, the band-pass signals are fed to block 58, where, in the present embodiment, the eight channel to 12-lead conversion is performed.

From this point in the diagram of FIG. 3, blocks 62, 64, 68, 70, and 72 describe data which are displayed on the user interface 20, as shown in FIGS. 4 through 17. Block 62 shows the instantaneous, real-time high frequency filtered QRS signal for each lead, updating with each new beat as that beat is incorporated into the average beat. Beats that are poorly cross-correlated are rejected and thus the template averages and the display will not be altered by such beats. The display is shown by element number 114 in FIG. 4.

Figure 8:
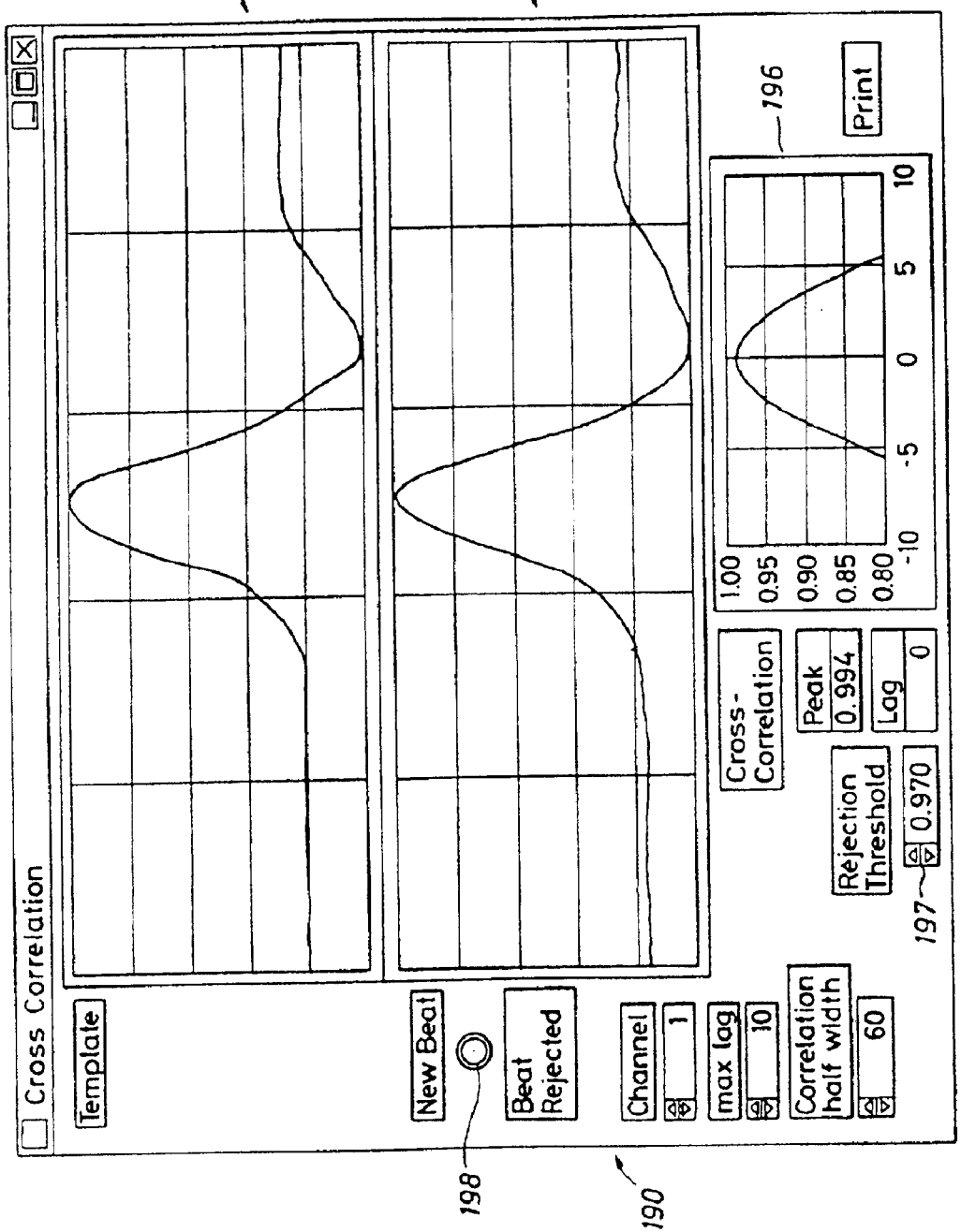
FIGS. 8 and 9 are real-time screen displays of cross correlation between a running, continuously updated waveform, or template, and a sensed waveform to determine departure from the template from one heartbeat to the next.
Figure 9:
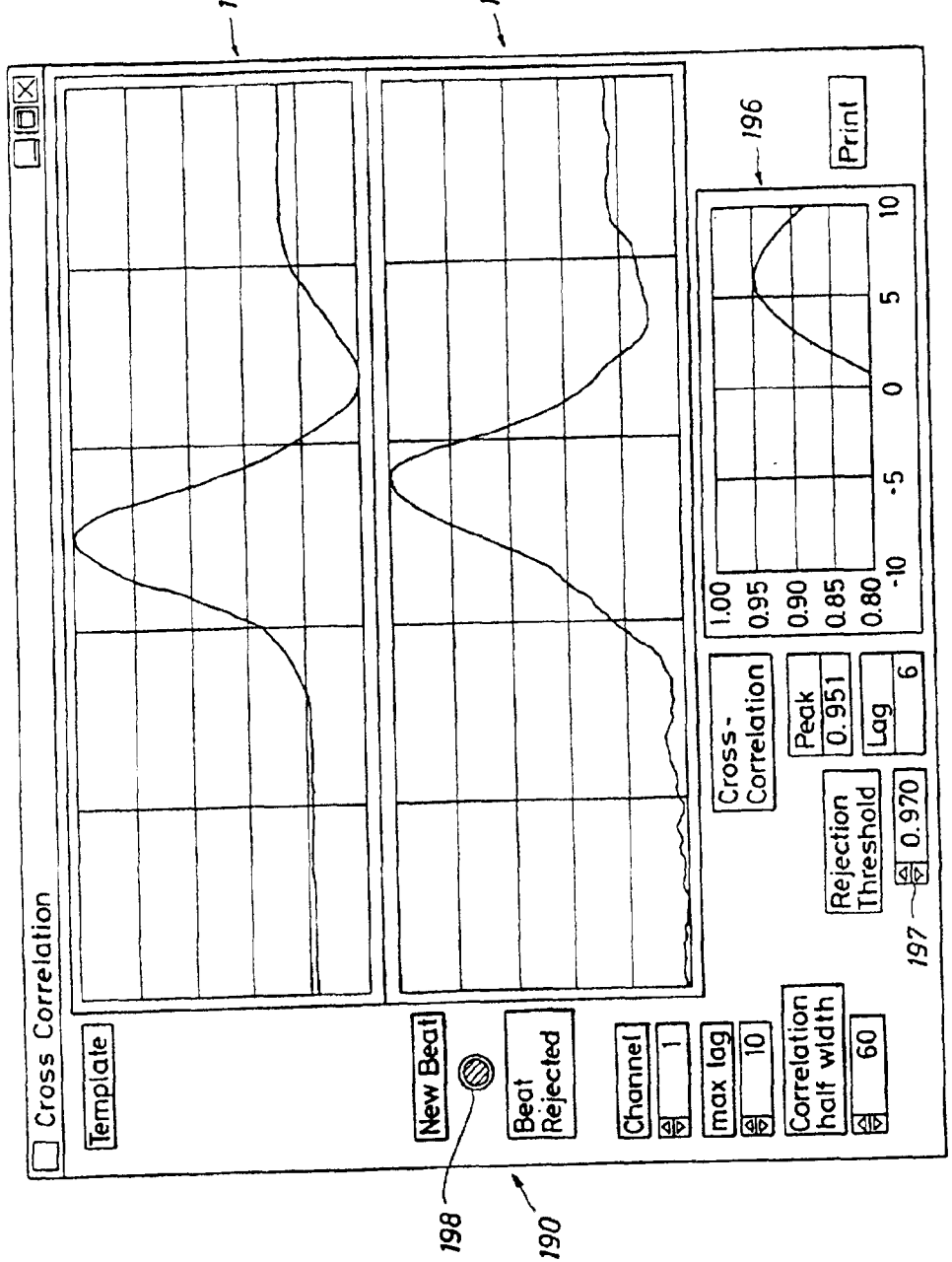

Block 64 determines the unfiltered QRS interval onset and offset automatically and in real time. This block receives an input from block 54 which detected and adjusted for any jitter in the well cross-correlated beats. The cross-correlation and jitter-correction from block 54 are therefore also displayed on the user interface, as shown in FIGS. 8 and 9. Block 68 describes the display of the instantaneous high frequency QRS RMS, HFQE and HFAV voltages and power spectrum generated for each lead using the unfiltered QRS interval onset and offset, and shown in FIG. 4 as element numbers 116 and 128.

Figure 10:
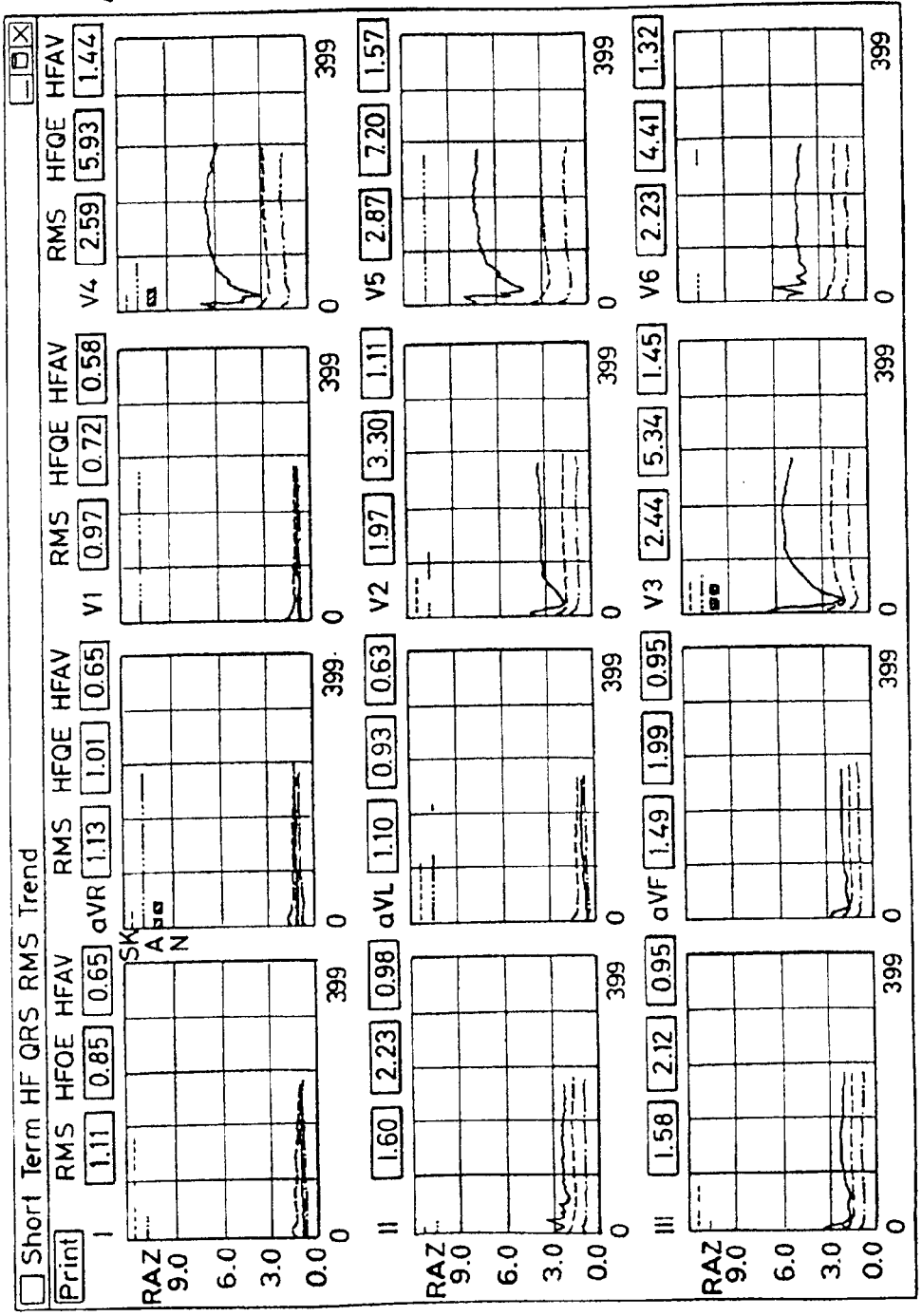
FIGS. 10 and 11 are real-time screen displays of short term trends of various data for a healthy subject and for a patient having known cardiac disease, respectively.

Block 70 describes the running plots of the RAZs ("go/no-go") as well as the voltages for the RMS, HFQE and HFAV of the high frequency QRS ECG signal versus time for each lead as depicted in FIGS. 10 through 13. FIGS. 10 (healthy subject) and 11 (subject with known coronary artery disease) depict short-term data trends whereas FIGS. 12 (healthy subject) and 13 (subject with known coronary artery disease) depict longer-term data trends. The horizontal (time) axis scale is user-adjustable on both the long and short-term trend plots, and can be shown either in beats (as depicted here) or in seconds. Clinicians can utilize these trends to assess how a monitored patient's cardiac function has changed over time, up to and including the present time. Specifically, clinicians can identify whether and when RAZs have developed or disappeared during the period of monitoring, as well the degree to which the RMS and related voltages of the high frequency QRS complex have changed over the same period of monitoring. Realization of such changes is particularly valuable to clinicians during situations when the presence or absence of incipient myocardial ischemia or infarction needs to be immediately identified, when the success or failure of invasive or noninvasive treatments administered for ischemia and infarction needs to be immediately recognized, and/or when cardiovascular responses during pharmacological or exercise stress tests or during a patient's ambulatory activities needs to be assessed.

Finally, block 72 describes another feature of the invention, online instantaneous RAZ detection for each lead. The presence of a "RAZ", or "reduced amplitude zone" within the envelope of the averaged high-frequency QRS signal, may be an indication of abnormal cardiac function. A RAZ, as originally defined by Abboud (but only in the context of off-line analyses), classically occurs when at least two local maxima of the upper envelope or two local minima of the lower envelope are present within the high frequency QRS signal. A local maximum or minimum is in turn defined as an envelope sample point (peak or trough) within the QRS interval wherein the absolute value of its voltage exceeds that of the three envelope sample peaks immediately preceding and following it. The RAZ is thus the region lying between the two neighboring maxima or minima. The present invention performs a real-time calculation, looking for local maxima and minima of the QRS envelope not only according to previously published off-line criteria of Abboud (i.e., "$RAZ_A$", or the Abboud RAZ) but also separately and especially according to new criteria that improve the specificity and accuracy of RAZ detection, particularly for the online setting.

One especially important modification contributing to such improvement is the requirement that the second, smaller local maximum within the high frequency QRS signal that defines the presence of the RAZ be at least two times, and optionally up to three to four times, larger in amplitude than the RMS "noise" of the high frequency signal that is present outside of the QRS interval (i.e., in any given chosen segment within the PR, ST or TP intervals). Another modification criterion implemented optionally by the user into the online RAZ detector is that the absolute value of the amplitude of the smaller of the two local maxima (or minima) constituting the RAZ must be at least a certain percentage of that of the larger of the two local maxima (or minima). These modifications as optionally implemented by the user within the present invention, together with the requirement that at least two local maxima of the upper envelope "and" (rather than "or") two local minima of the lower envelope be present to constitute a RAZ, are collectively referred to as the criteria that define the "NASA RAZ", or "$RAZ_N$".

Yet another novel set of user-selectable criteria used in the present invention to assess the presence or absence of a "statistical" type of RAZ concerns the use of real-time calculation of the both the skewness and the kurtosis of the incoming high frequency QRS signal. When present, the skewness-kurtosis type of RAZ is referred to as the $RAZ_{S-K}$. The presence of a $RAZ_A$, $RAZ_N$, and/or $RAZ_{S-K}$ by "go/no-go" indicators on the display, as shown by element 117 in FIG. 4, may also be displayed as a running parameter with time, in a manner similar to FIGS. 10–13.

Figure 4:
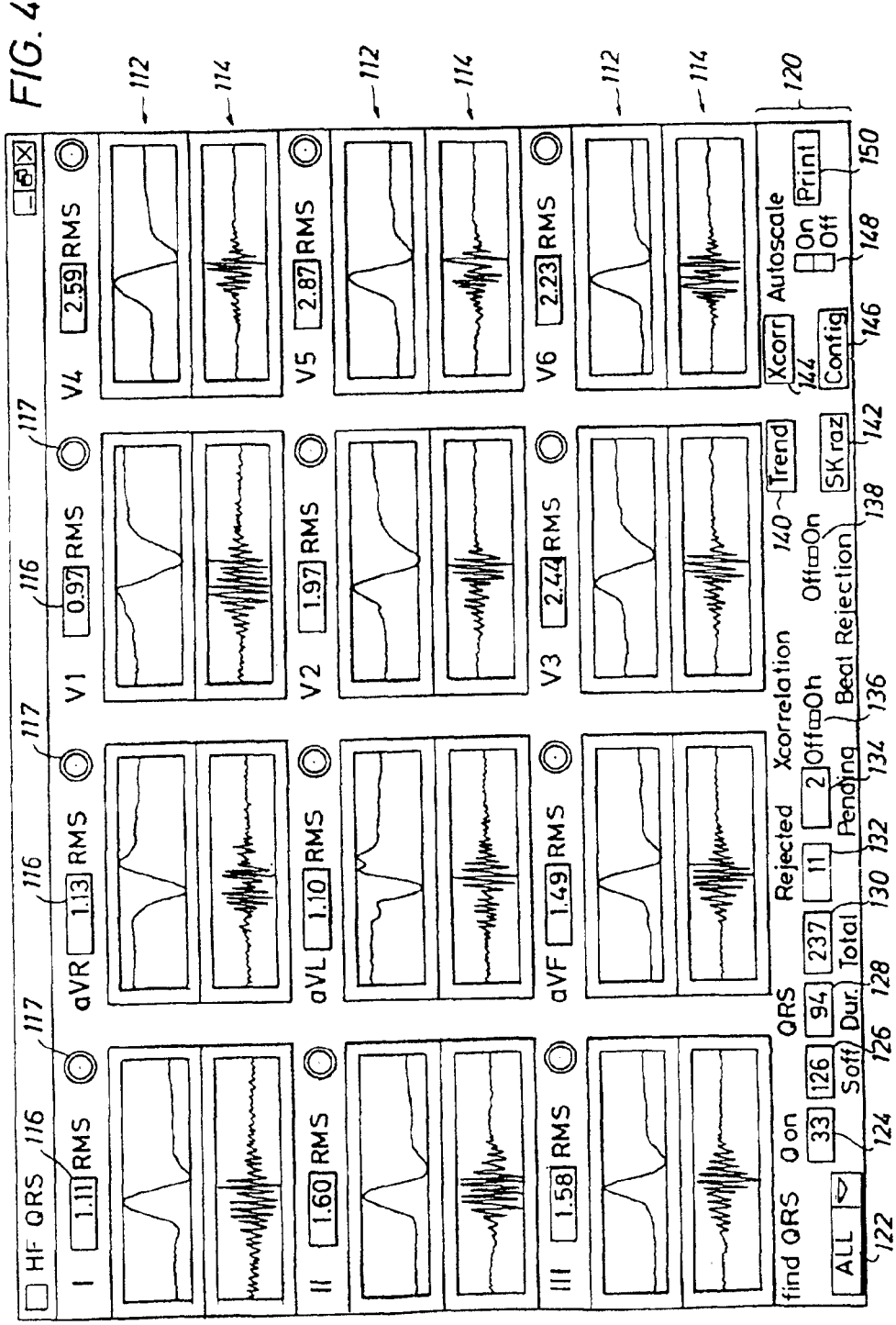
FIG. 4 is a real-time screen display, showing characteristic data obtained from a healthy subject, including a side-by-side display of a standard ECG and a filtered (high frequency) ECG.
Figure 5:
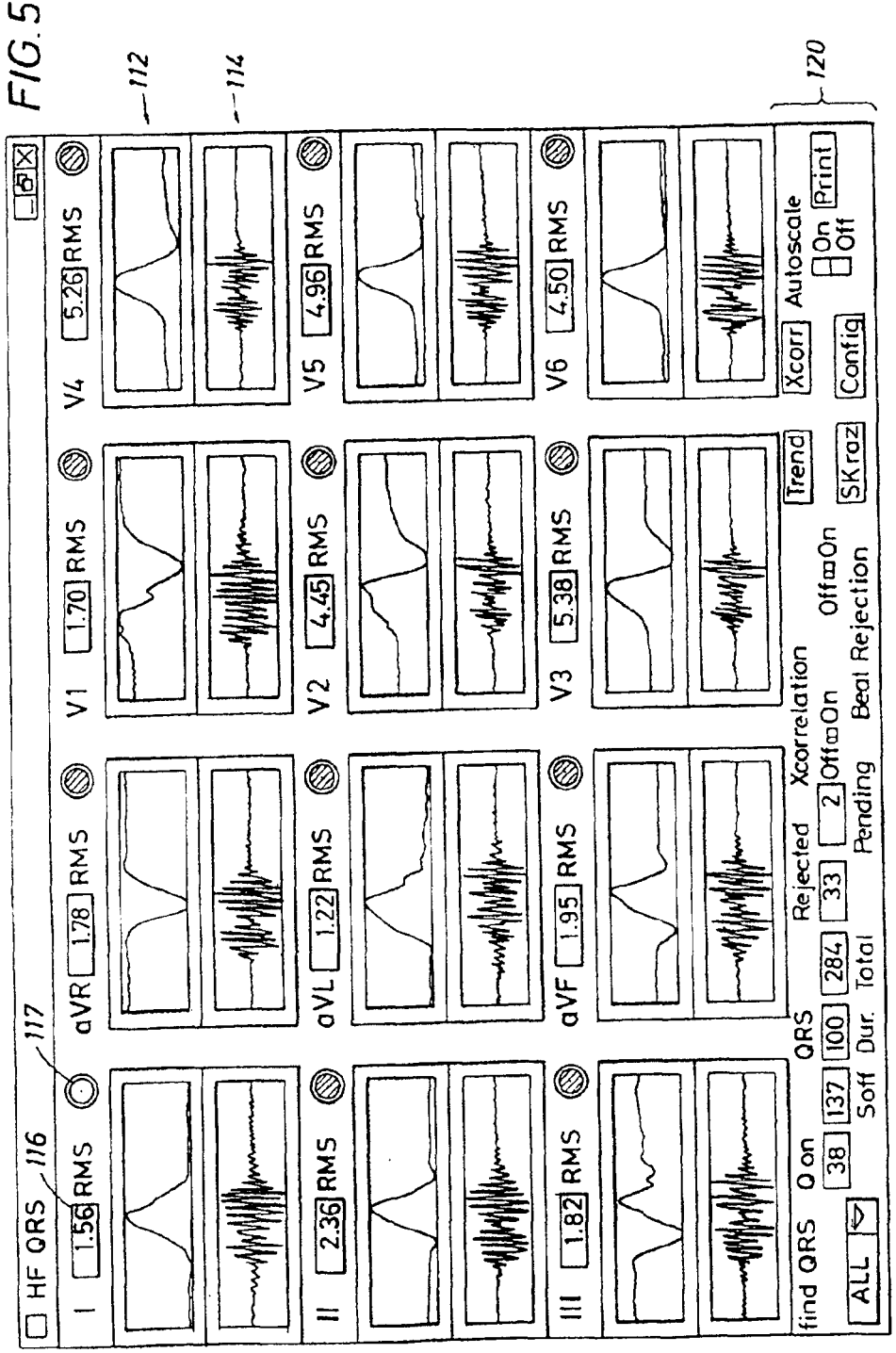
FIG. 5 is a real-time screen display, showing characteristic data obtained from a patient having known cardiac disease, including a side-by-side display of a standard ECG and a filtered ECG.

Referring now more particularly to FIGS. 4 and 5, a feature of the present invention is the simultaneous display in real-time of various aspects of cardiac function with respect to both the conventional and high frequency QRS ECG. Further, the present invention provides simultaneous, side-by-side or vertical displays of that data to provide the clinician with a tool to compare these aspects of the ECG with one another for a more complete picture of cardiac function than has been previously available. The present invention also displays the conventional and high frequency 12-lead configurations on one user interface display, while displaying the presence or absence of RAZs on the same display to alert the clinician to potentially abnormal cardiac function.

The display of FIGS. 4 and 5 includes a conventional, low frequency ECG signal, designated by the element number 112. The display signal 112 includes the signals from leads I, II, III, aVR, aVL, aVF, and V1–V6 in the conventional manner. Further, the display signal 112 slides from left to right, updated with each beat, also in the conventional manner, as a reference for the clinician. Positioned immediately adjacent to or below the conventional ECG display 112 is a display 114 of a running, instantaneous filtered (i.e. high frequency) QRS ECG signal, one for each of the twelve leads, corresponding to the individual leads of the display 112. The display signal 114 includes the signals from leads I, II, III, aVR, aVL, aVF, and V1–V6 to correspond to like signals in the display 112. Above each high frequency QRS signal is the instantaneous RMS value 116 in that particular lead, and an instantaneous RAZ indicator 117, defaulted to the RAZ type of the user's choice (in this case the $RAZ_N$).

At the bottom of the screen display of FIGS. 4 and 5 is a tool bar 120. The tool bar 120 provides user control and display of various data useful to the clinician. The tool bar includes a user selectable indicator 122 in which the user can select which of a plurality of QRS complexes to capture. Displays 124, 126, and 128 show the timing of the QRS onset, QRS offset, and the duration of the QRS complex, respectively. A display 130 shows the total number of heartbeats which have been detected during any particular run, while a display 132 shows the number of beats rejected and a display 134 shows the number of beats whose processing is pending, if any. Toggle buttons 136 and 138 permit the user to turn on and turn off the cross correlation function and the beat rejection function, respectively. Display buttons 140, 142, 144, and 146 permit the user to select other displays for the screen, as shown. A toggle button 148 permits the user to turn on and turn off an autoscale function, and a print button 148 permits the user to print a particular screen capture at his discretion.

Of particular note, in comparing FIGS. 4 and 5, is the small number of reduced amplitude zones and lit RAZ indicators 117 for the healthy patient shown in FIG. 4, versus the much larger number of reduced amplitude zones and lit RAZ indicators for the subject with known coronary artery disease, shown in FIG. 5.

Figure 6:
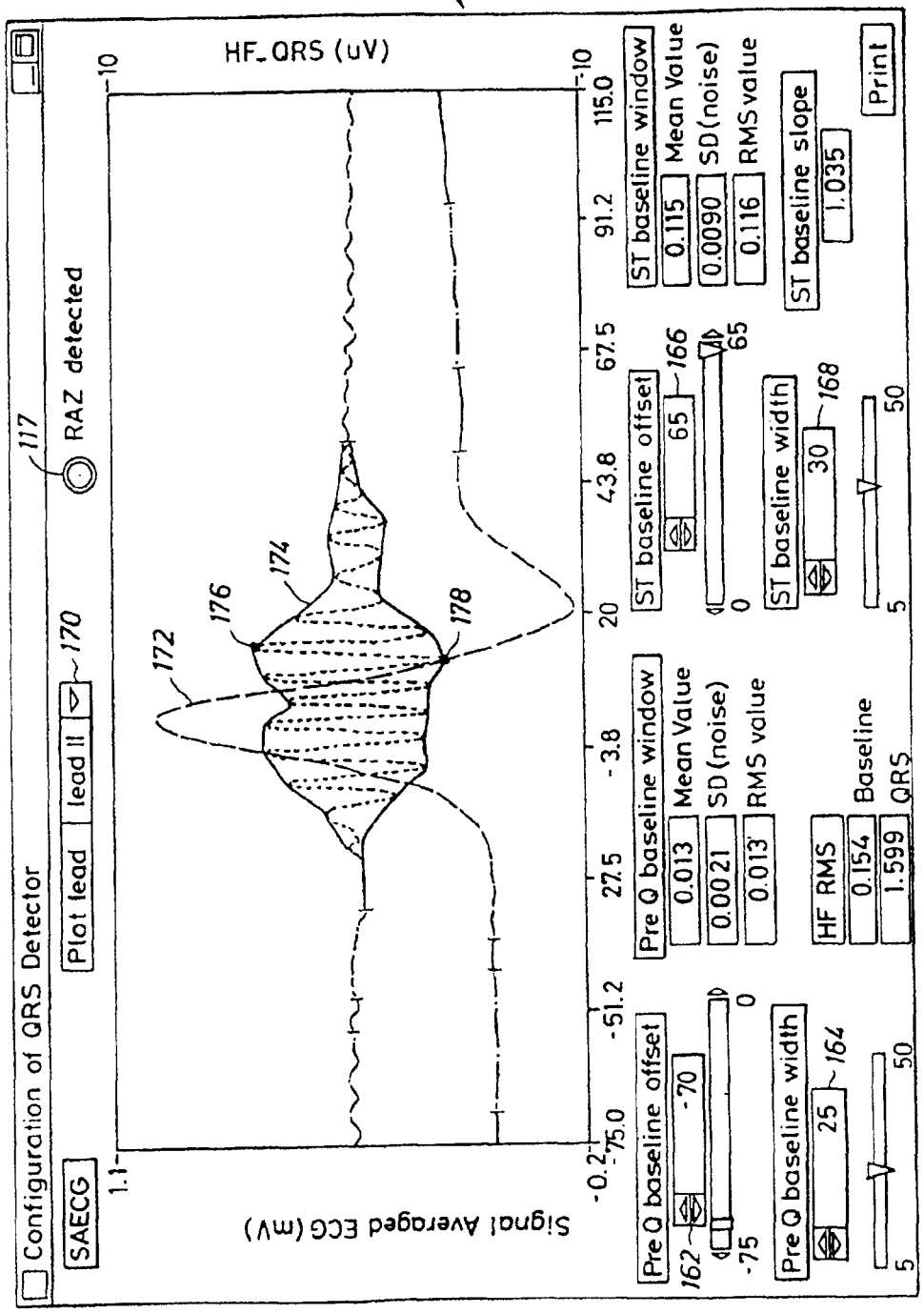
FIGS. 6 and 7 are real-time screen displays, showing the configuration of a QRS detector for a normal, healthy subject and for a patient having known cardiac disease, respectively.
Figure 7:
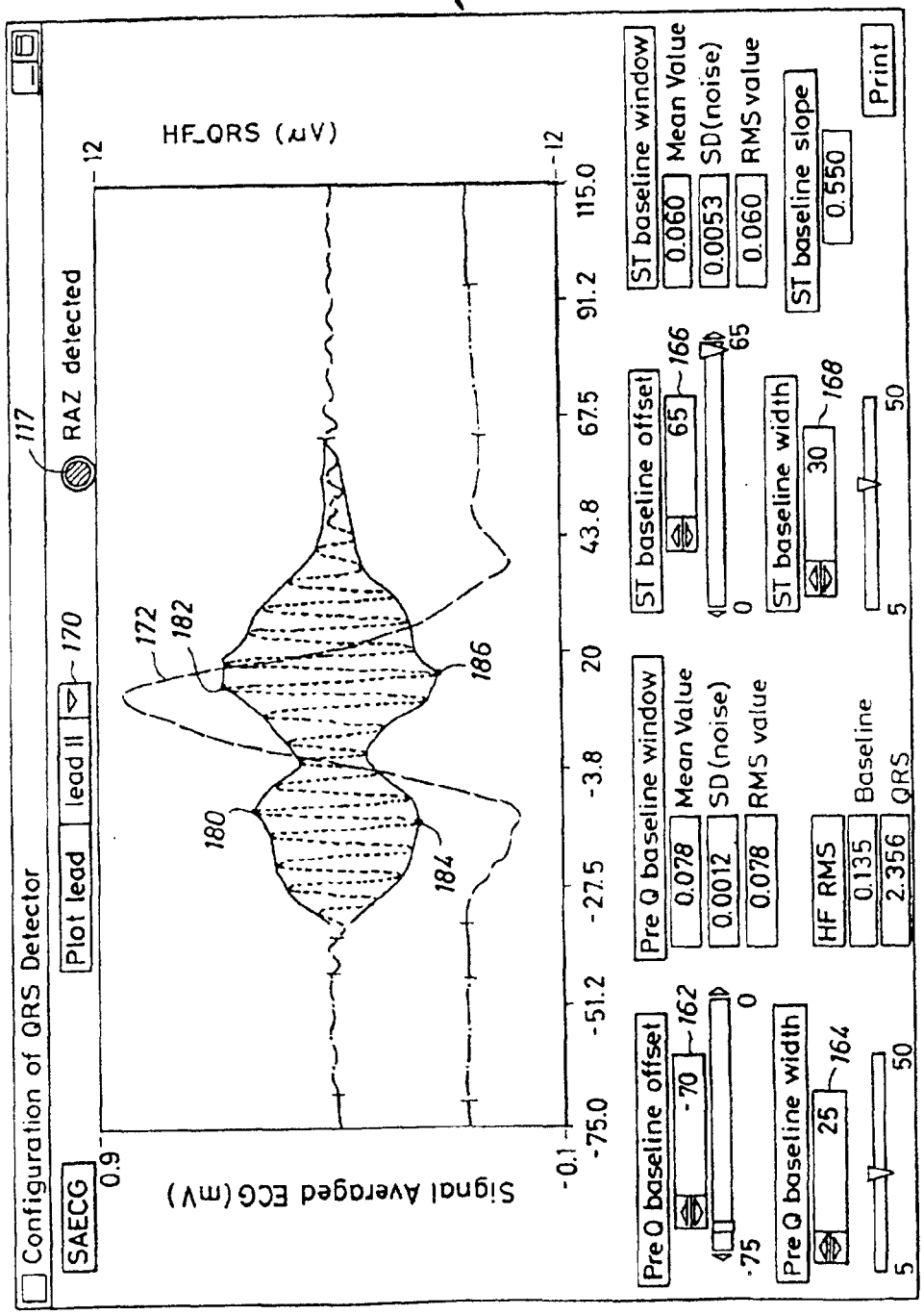

FIGS. 6 and 7 show configuration screen 160 for the online QRS interval detector of the invention, selectable by button 146 of FIGS. 4 and 5. The configuration screen of FIGS. 6 and 7 permits the user to select a period within the P-R interval of the ECG, with specific pre-Q offset and interval width selectors 162 and 164, respectively, that will aid in the determination of the onset of the QRS complex. The values for these parameters shown in FIGS. 6 and 7 have been selected based on initial experience to provide satisfactory performance of the invention for the broadest array of subjects, since cardiac function typically varies from patient to patient. Similarly, selectors 166 and 168 permit the user to select the offset and width, respectively, of a portion of the ST segment that will aid in the determination of the offset of the QRS complex. The configuration screen 160 also displays various parameters measured from the current heartbeat, as shown. An indicator 170 shows the user which of the leads is selected, in the case of FIGS. 6 and 7 that lead is lead II. A RAZ indicator 117 is also provided for the convenience of the user.

FIGS. 6 and 7 also include superimposed displays of a low frequency signal averaged ECG 172 and an averaged high frequency filtered signal 174. The ordinate on the left of FIGS. 6 and 7 shows the averaged low frequency signal 172 in millivolts, and the ordinate on the right shows the averaged high frequency signal 174 in microvolts.

FIG. 6 shows a single local maximum 176 and a single local minimum 178. However, FIG. 7, depicting the waveforms for a patient with known coronary artery disease, shows two local maxima 180 and 182, and two local minima 184 and 186. Since the maxima and/or minima occur within the QRS complex, and are separated by at least three envelope sample points with lesser absolute amplitudes between them, they define a reduced amplitude zone as also shown on the lit RAZ indicator 117.

FIGS. 8 and 9 depict cross correlation screens 190 of the invention. The screen 190 is selected by a user with button 144 (FIG. 4). The screen includes a display 192 of a template, averaged over a user selectable number of beats. A display 194 shows the low frequency ECG of the current beat, and a display 196 shows the cross correlation between the waveforms of display 192 and display 194. A user may select the threshold for the cross correlation, below which the beat is rejected, by a selector 197 and, if a beat is rejected, an indicator light 198 illuminates.

Note that in FIG. 9 the current heartbeat shown on the display 194 is noisy and has a different shape than the template. The current beat is also shifted in time from the template of display 192. Consequently, the cross correlation between them is poor, as reflected in the display 196, which only has a peak of 0.951 (i.e. below the user selectable threshold set at 0.970 in this case) and the beat is rejected, as shown by the indicator light 198. Thus, the current beat is not incorporated into the running template of the averaged ECG.

Figure 11:
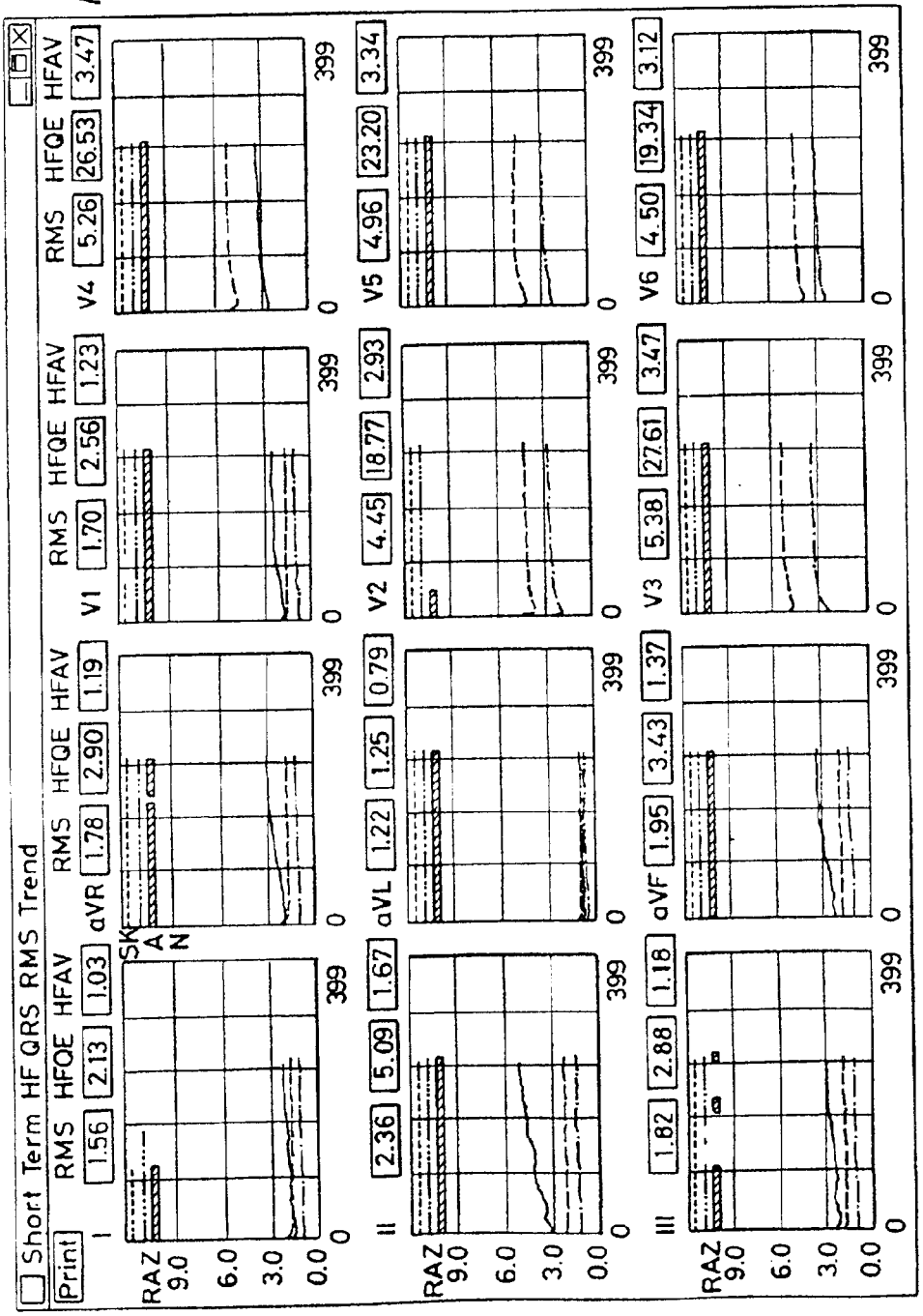
Figure 12:
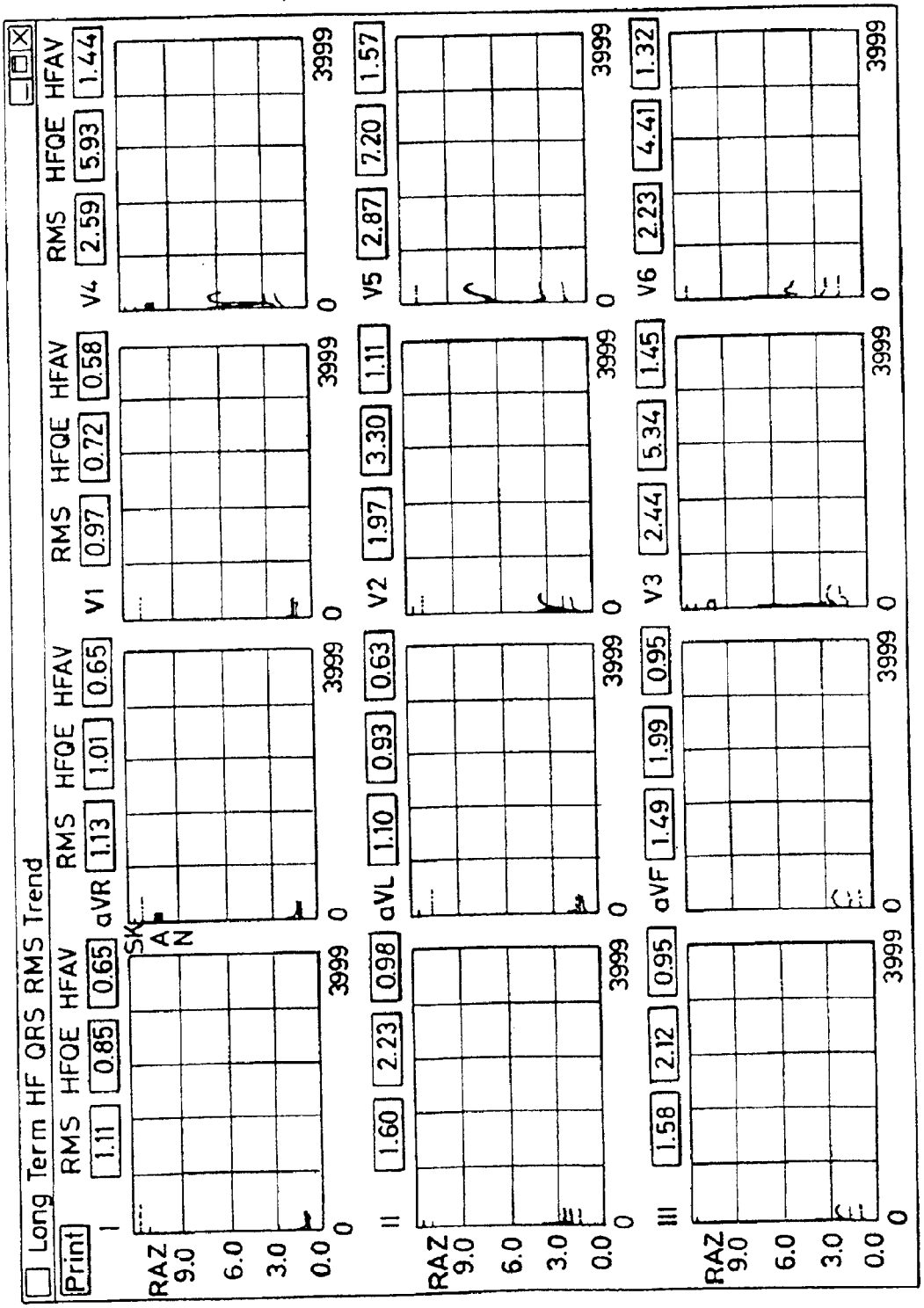
FIGS. 12 and 13 are real-time screen displays of long term trends of various data for a healthy subject and for a patient having known cardiac disease, respectively
Figure 13:
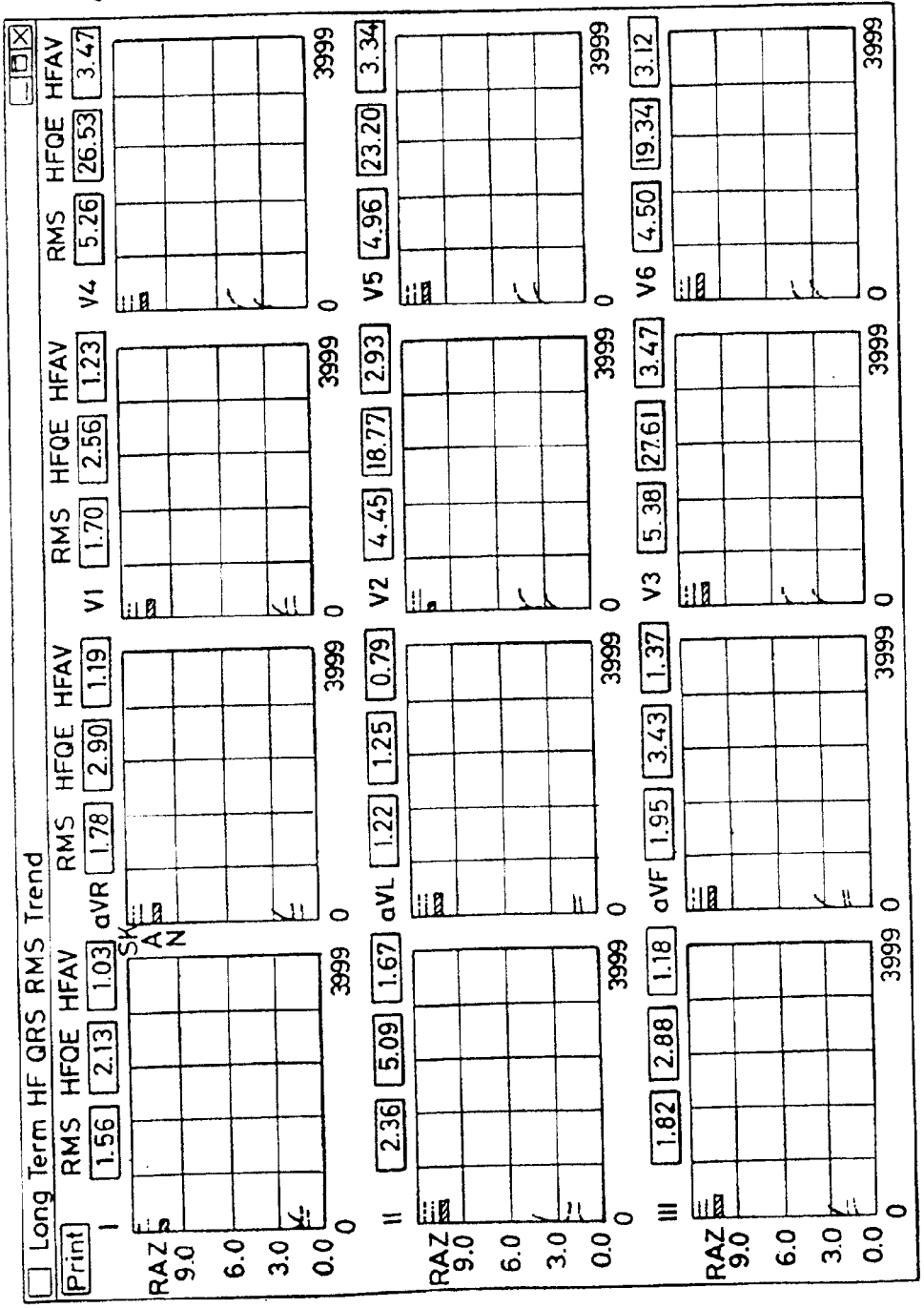

FIGS. 10 through 13 depict trend lines for the RMS, HFQE, and HFAV, as well as show the current value for these parameters. These displays further include lines depicting the presence versus the absence of three types of RAZ as described herein. These displays illustrate another feature of the present invention, that of showing a trend of parameters over time. Specifically, the trend lines shown on a screen 200, which are continuously updated in real time, illustrate the presence (versus the absence) of all three types of RAZs over a user-selectable period of time (always up to and including the present time) as well as the voltage trends for RMS, HFQE and HFAV over this same user-selectable period of time for all the leads attached to the patient. FIGS. 10 and 11 provide examples of trend lines on a short-term time scale for a healthy subject and for a patient with known coronary artery disease, respectively, whereas FIGS. 12 and 13 provide corresponding examples of trend lines on a long-term time scale for these same individuals. The short and long-term trend line plots can be accessed simultaneously by the user, and, to reiterate, the time intervals (horizontal axes depicted here in units of beats) on both plots are completely selectable by the user. The particular parameters depicted on these plots are intended to be illustrative only, and other parameters may be similarly illustrated. The ordinate for each plot is in microvolts with respect to the RMS, HFQE and HFAV (the RAZs are unitless, "go versus no-go" entities), whereas the abscissa can be in either beats or seconds, for characterization of the trend.

Numerical measures of the high frequency QRS ECG may be calculated in several ways. These measures are important because they often decrease when ischemia is present. Perhaps the most popular measure is the root mean square (RMS) voltage of the QRS signal, which is equivalent to the "area under the curve" of the power spectrum, defined as $$RMS = \sqrt{\frac{\sum_{i=ufqon}^{ufqoff} X_i^2}{UFQRSD}}$$

where $X_i$ is the filtered voltage at a given sampling point, ufqon and ufqoff are the onset and offset, respectively, of the QRS interval, and UFQRSD is the unfiltered QRS interval duration as defined by ufqon and ufqoff. In this context, the term "onset" means the start of the QRS interval, and the term "offset" means the end of the QRS interval. This is the primary numerical measure used in preferred embodiment of the present invention.

Other numerical measures of the high frequency QRS signal have also been proposed (and used strictly in an off-line fashion) by Xue et al. (see Xue, Q., B. R. Reddy, and T. Aversano. Analysis of high-frequency signal-averaged ECG measurements. *J Electrocardiol* 28: 239–45, 1995). These numerical measures include the high frequency integral of absolute values (HFAV) and the high frequency QRS energy (HFQE). Xue et al. have defined HFAV and HFQE as follows:

$$HFAV = \sum_{i=uqon-10\,ms}^{uqoff+10\,ms} |X_i - AVNL|$$

and, $$HFQE = \sum_{i=uqon-10\,ms}^{uqoff+10\,ms} (X_i - AVNL)^2$$

wherein AVNL equals the average noise level of the filtered signal in the ST segment in a 40 ms window located 60 ms from the QRS offset. It should be noted that in their own definitions for HFAV and HFQE (as shown above), Xue et al. "pad" both the QRS onset and offset by extra 10 ms each in an effort to reduce noise and noise variability, presumably to compensate for potential inaccuracies and inconsistencies related to the determination of the QRS interval.

In the presently preferred embodiment of the present invention, the definitions for HFAV and HFQE are modified in two ways. First, because the present invention provides a means of viewing the high and low frequency ECG signal in real time, thereby providing reliability for the determination of the QRS interval, the necessity (or lack thereof) of using the 10 millisecond padding periods is left to the discretion of the user. Second, the present invention preferably uses the PR interval or TP segment rather than the ST segment to determine the AVNL of the baseline, since a segment of the cardiac cycle wherein neither depolarization nor repolarization is present is preferred. In the device of the present invention disclosed herein, AVNL is determined as the RMS noise of the filtered signal that is within a 25 ms interval in the PR segment.

In the preferred embodiment, HFAV is measured as:

$$HFAV = \sum_{i=uqon}^{uqoff} |X_i - AVNL|$$

wherein AVNL (average noise level) equals the "noise" of the high frequency (i.e., filtered) signal within that portion of the PR interval just noted.

Further, high frequency QRS energy (HFQE) is calculated as:

$$HFQE = \sum_{i=uqon}^{uqoff} (X_i - AVNL)^2$$

wherein AVNL is determined in the same way as for HFAV.

Figure 14:
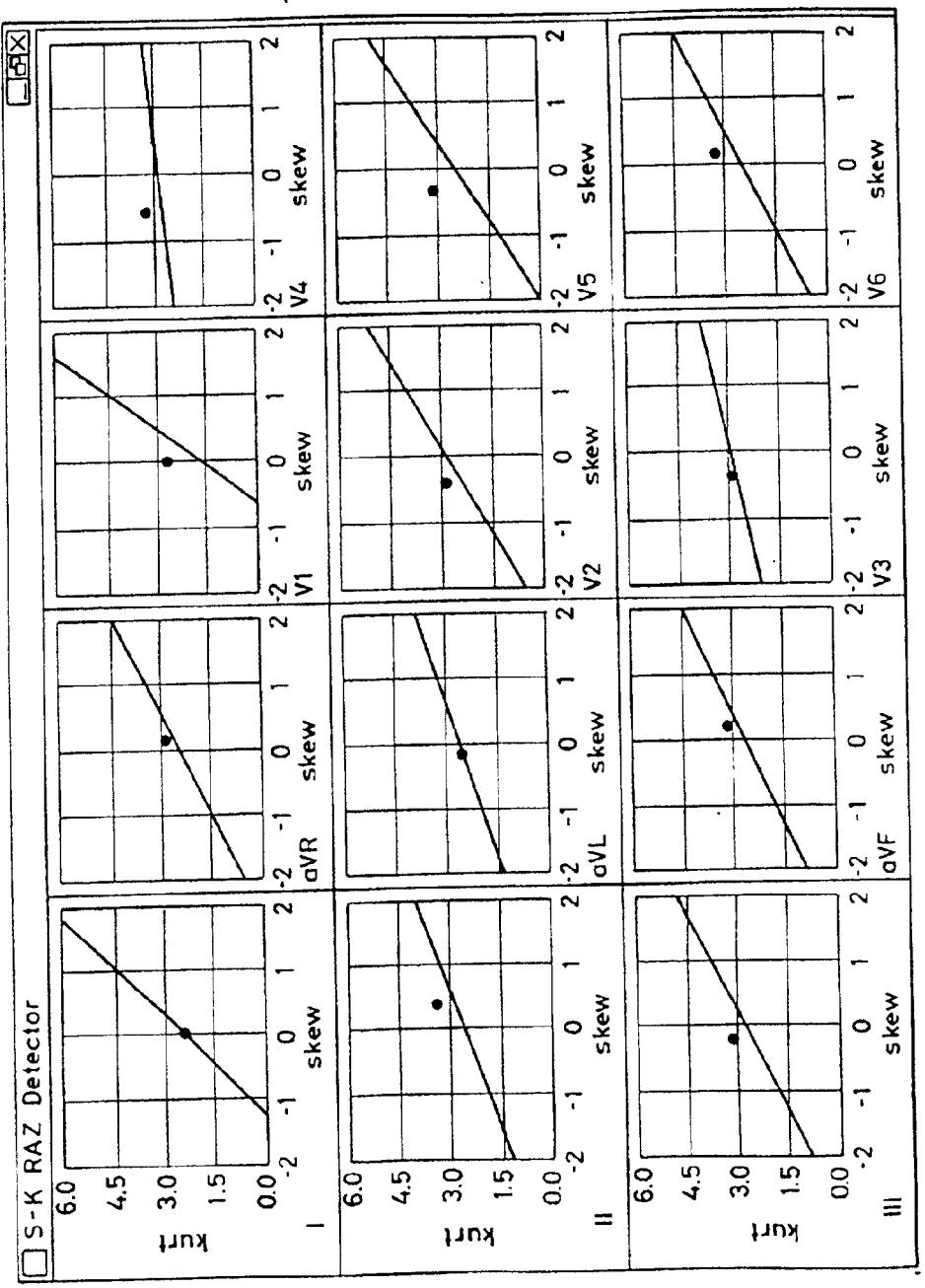
FIGS. 14 and 15 are real-time screen displays of high frequency QRS skewness versus kurtosis for a healthy subject and for a patient having known cardiac disease, respectively.
Figure 15:
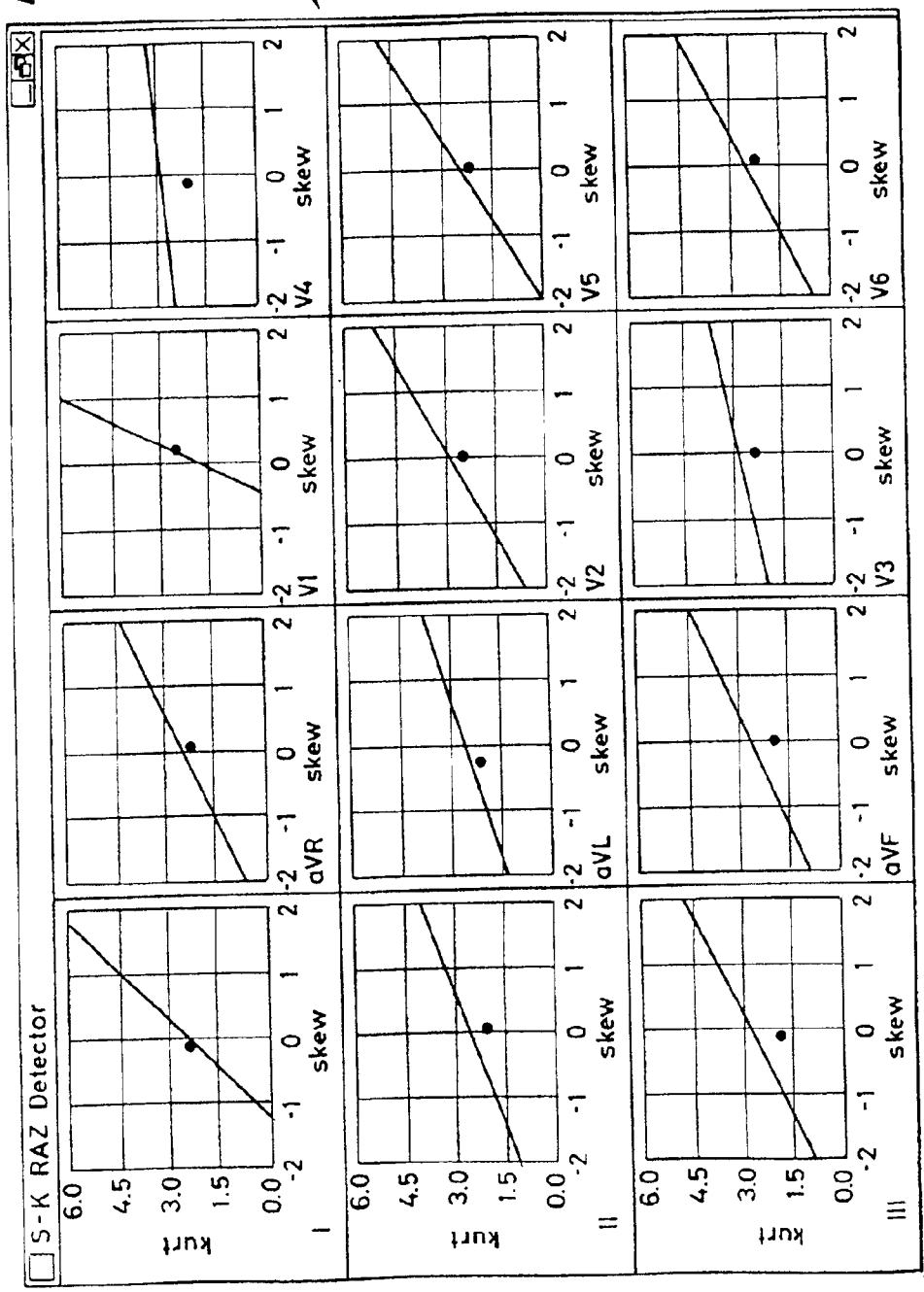

A useful characterization of a set of data includes skewness and kurtosis. Skewness is a measure of symmetry, or more accurately, the lack of symmetry. A distribution, or data set, is symmetric if it looks the same to the left and right of the center point. Kurtosis is a measure of whether the data are peaked or flat relative to a normal distribution. That is, data sets with a high kurtosis tend to have a distinct peak near the mean, decline rather rapidly, and have heavy tails. Data sets with low kurtosis tend to have a flat top near the mean rather than a sharp peak. A uniform distribution would be the extreme case. By displaying skewness values alone, kurtosis values alone, or skewness versus kurtosis graphically with one value on the ordinate and the other on the abscissa, the clinician may obtain information from the high frequency QRS signals potentially indicative of cardiac disease. Referring to FIGS. 14 and 15, a display 250 is provided to show real-time, continuously updated plots of skewness versus kurtosis against a background line of a normal population distribution function. If a patient's S-K data in any given lead fall on or above that lead's distribution function, the data for that lead are considered "normal", as shown in most of the leads of FIG. 14, whereas data from any given lead falling below that lead's distribution function, as shown in most of the leads of FIG. 15, provides a visual indication of potential cardiac disease, i.e., a positive "$RAZ_{S-K}$".

Figure 16:
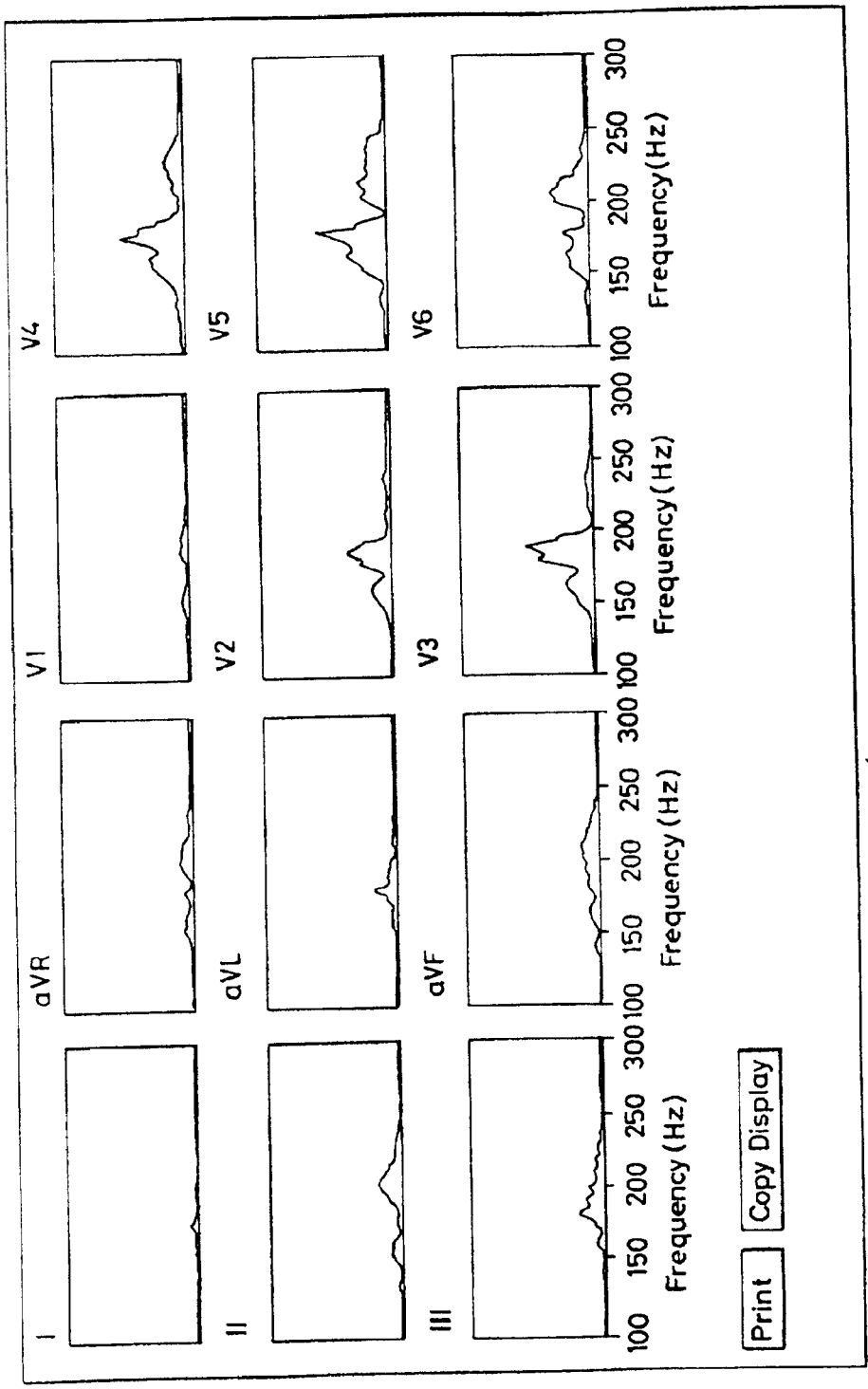
FIGS. 16 and 17 are real-time screen displays of the spectrum of power for normal and diseased patients, respectively.
Figure 17:
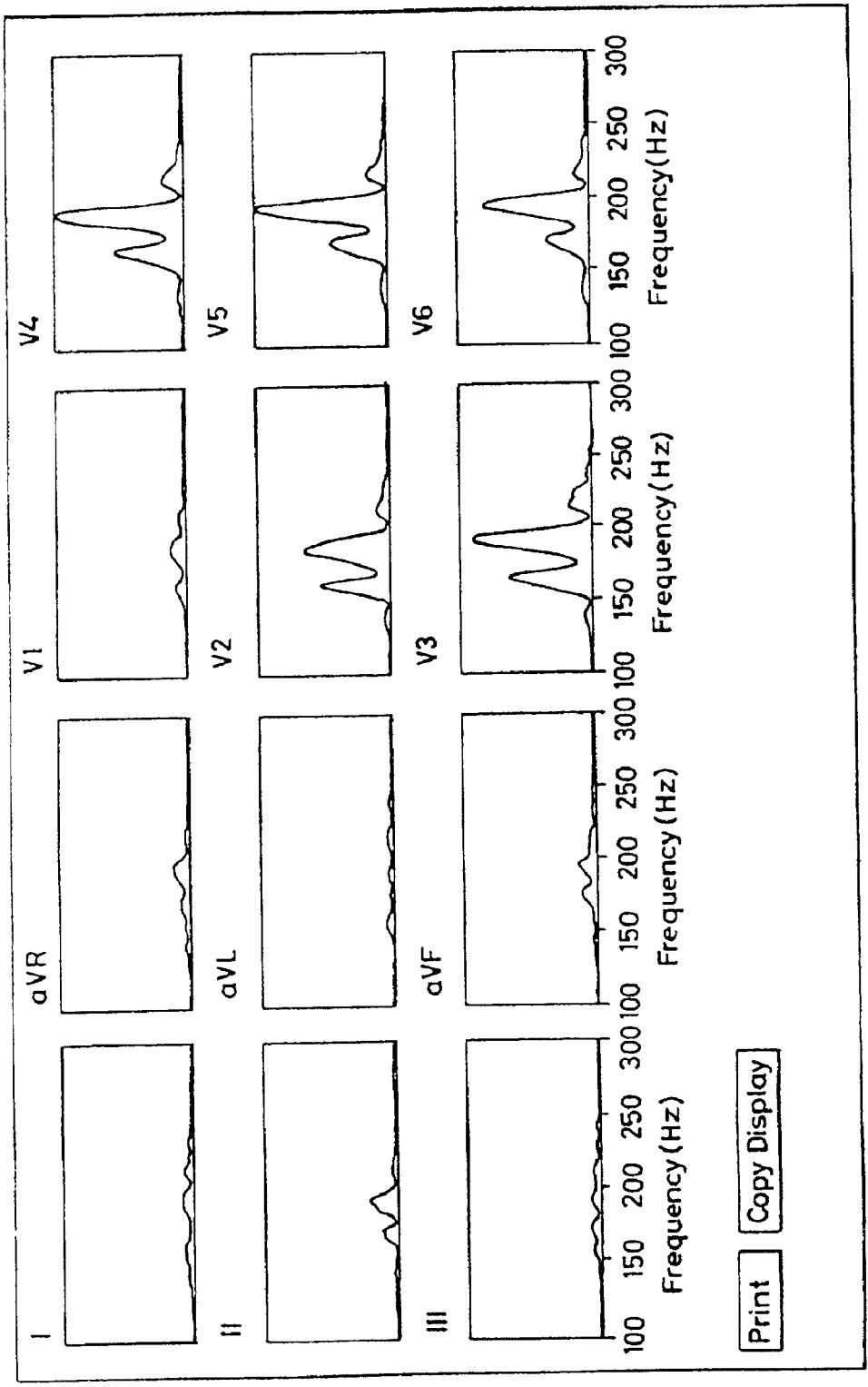

Referring now to FIGS. 16 and 17, a display 270 is provided to show the power spectrum of the high frequency QRS signal for each lead. A change in the shape of the spectral plot such that two distinct peaks occur rather than one may be further indication of cardiac malfunction.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

We claim:

1. A method of monitoring cardiac function, comprising the steps of:
    a. sensing an electrocardiograph signal, the signal comprising a succession of waves;
    b. independently identifying the QRS complex with each successive wave continuously, in real time, and in a beat-by-beat manner;
    c. independently analyzing data from the succession QRS complexes relating to the cardiac function continuously, in real-time, and in a beat-by-beat manner, wherein the step of analyzing is comprised of band-pass filtering the data in a high frequency range between about 150 Hz and about 250 Hz; and
    d. displaying predetermined characteristics of all data contiuously, in real-time, and in beat-by-beat manner.

2. The method of claim 1, further comprising the steps of developing measures related to the data from the succession QRS complexes and wherein the step of displaying is comprised of displaying the measures on a monitor.

3. The method of claim 1, wherein the step of analyzing is further comprised of:
    generating an initial template of the signal using the first QRS complex from the first wave of the signal;
    cross-correlating each subsequent independently identified QRS complex continuously and in a beat-by-beat manner aginst predetermined criteria wherein accepted QRS complexes are incorporated into the initial template to create a running signal average template in real-time;
    aligning each independently identified QRS complex with the running signal average template continuously, in real-time, and in a beat-by-beat manner; and
    calculating predetermined, selectable high frequency characteristics from the running signal average template in a continuous, beat-by-beatm, real-time manner.

4. The method of claim 3, wherein the step of calculating is comprised of calculating a reduced amplitude zone,
    wherein the reduced amplitude zone occurs when at least two local maxima or at least two local minima are present in the filtered data; and
    wherein each local maximum or each local minimum is a peak or a trough, respectively and wherein the absolute value of each peak or trough's voltage exceeds that of a predetermined number of sample points within the filtered data immediately preceding and following each peak or trough.

5. The method of claim 4, wherein the absolute value of the amplitude of the smallest of the at least two local maxima or the smallest of the at least two minima is at least a predetermined percentage relative to the largest of the at least two maxima or the largest fo the at least two minima, respectively.

6. The method of claim 4, wherein the absolute value of the amplitude of the smallest of the at least two local maxima or the smallest of the at least two local minima is at least a predetermined multiple of the high frequency noise level of a predetermined iso-electric portion.

7. The method of claim 3, wherein the step of calculating is comprised of calculating a skewness, kurtosis, or both of the filtered data.

8. The method of claim 1, wherein the step of displaying is comprised of displaying the sensed signal from step 1.a. adjacent the data from step 1. d. on a monitor.

9. The method of claim 1, wherein the step of analyzing is further comprised of computing the presence or absence of reduced amplitude zones from the high frequency filtered data associated with the QRS complex.

10. The method of claim 9, wherein the step of displaying is comprised of displaying the presence or absence of the reduced amplitude zones on a monitor.

11. An electrocardiograph system for monitoring cardiac function comprising:
    a. means for sensing an electrocardiograph signal, the signal comprising a succession of waves;
    b. means for independently identifying the QRS complex with each successive wave, continuously, in real-time, and in a beat-by-beat manner;
    c. means for independently analyzing data from the successive QRS complexes relating to the cardiac function continuously, in real-time, and in a beat-by-beat manner, wherein the means for analyzing is comprised of a means for band-pass filtering the data in a high frequency range between about 150 Hz and about 250 Hz; and
    d. means for displaying predetermined characteristics of all data continuously, in real-time, and in a beat-by-beat manner.

12. The system of claim 11, wherein the means for displaying is comprised of displaying the sensed signal from step 9.a. on a monitor adjacent the data of step 9.d.

13. The system of claim 11, wherein the means for analyzing is further comprised of a means for computing the presence or absence of reduced amplitude zones from the succession of high frequency QRS complexes.

14. The system of claim 11, wherein the means for displaying all data comprises a monitor.

15. An electrocardiograph system comprising:
   a. at least one electrode adapted to sense a conventional electrocardiogram signal comprising a succession of waves;
   b. an electrocardiogram console adapted to receive the conventional electrocardiogram signal from the at least one electrode and to independently identify the QRS complex with each successive wave continuously, in real-time, and in a beat-by-beat manner at at least the Nyquist rate;
   c. a computer coupled to the console to receive the conventional electrocardiogram signal, to band-pass filter data from the succession of QRS complexes in a high frequency range, and to indepently analyze the filtered data from the succession of QRS complexes continuously, in real-time, and in a beat-by-beat manner; and
   d. a monitor to display predetermined characteristics fo all data continuously, in real time, and in a beat-by-beat manner.

16. The system of claim 15, wherein the monitor is further adapted to display the conventional electrocardiogram signal and the predetermined characteristics of filtered data, analyzed data, or both adjacent one another in real time.

17. The system of claim 16, wherein the computer's ability to analyze the filtered data is comprised of calculating the presence or absence of reduced amplitude zones.

18. The system of claim 17, wherein the monitor is further adapted to display the presence or absence of the reduced amplitude zones.

19. The system of claim 15, wherein the computer's ability to analyze the filtered data is comprised of calculating a real time cross correlation function from the succession of waves.

20. The system of claim 15, wherein the computer's ability to analyze the filtered data is comprised of generating a running a QRS template based on a user selectable number of waves.

21. A display the electrocardiograph signal and data resulting from the method described in claim 1 comprising:
   a. a plot of at least one real-time low frequency component of the electrocardiogram signal; and
   b. a plot of at least one real-time high frequency component of the electrocardiogram signal derived from the filtered data, analyzed data, or both, wherein the plot of the at least one real-time low frequency component displayed adjacent the plot of the at least one real-time high frequency component.

22. The display of claim 21, wherein the plot of the at least one real-time low frequency component electrocardiogram signal comprises a plurality of plots of real-time low frequency components of a plurality of electrocardiogram signals and the plot of the at least one real-time high frequency component of the electrocardiogram signal comprises a plurality of plots of real-time high frequency components of a plurality electrocardiogram signals.

23. The display of claim 21, wherein the low frequency and high frequency components of the electrocardiograph signal are a representation of cardiac function in real-time.

24. The display of claim 21, further comprising user selectable controls to alter the display.

25. The display of claim 21, further comprising at least one indicator for the presence or absence of a reduced amplitude zone.

26. The display of claim 21, further comprising at least one plot of user selectable data measured over time.

27. The display of claim 26, wherein the user selectable data are selected from the group consisting of root mean square voltage values, high frequency energy (HFQE), high frequency integral of absolute value (HFAV), $RAZ_A$, $RAZ_N$, and $RAZ_{S-K}$.

28. A method of monitoring cardiac function, comprising the steps of:
   a. sensing an electrocardiograph signal, the signal comprising a succession of waves;
   b. independently identifying the QRS complex with each successive wave continuously, in real-time, and in a beat-by-beat manner;
   c. indepently analyzing data from the succession of QRS complexes, wherein the step of analyzing is comprised of band-pass filtering the data in high frequency range between about 150 Hz and about 250 Hz, and evaluating the filtered data for the presence or absence of a reduced amplitude zone continuously, in real-time, and in a beat-by-beat manner; and
   d. displaying predetermined characteristics of all data continuously, in real-time, and in a beat-by-beat manner on a monitor.

29. The method of claim 28, wherein the step of displaying is further comprised of displaying the presence or absence of the reduced amplitude zones on the monitor.

30. An electrocardiograph system comprising:
   a. means for sensing an electrocardiograph signal, the signal comprising a succession of waves;
   b. means for independently identifying the QRS complex with each successive wave continuously, in real-time, and in a beat-by-beat manner;
   c. means for independently analyzing data from the succession of QRS complexes relating to the cardiac function, wherein the step of analyzing is comprised of band-pass filtering data in a high frequency range between about 150 Hz and about 250 Hz, and evaluating the filtered data for the presence or absence of reduced amplitude zones continuously, in real-time, and in a beat-by-beat manner; and
   d. means for displaying predetermined characteristics of all data continuously, in real-time, and in a beat-by-beat manner on a monitor.

31. A method of monitoring cardiac activity, comprising the steps of:
   a. sensing an electrocardiograph signal, the signal comprising a succession of waves;
   b. independently identifying the QRS complex with each successive wave continuously, in real-time, and in a beat-by-beat manner;
   c. independently analyzing data on a computer processor of known type from the succession of QRS complexes relating to the cardiac activity continuously, in real-time, and in a beat-by-beat manner, the step of analyzing is comprised of band-pass filtering the data in a high frequency range between about 150 Hz and about 250 Hz; and
   d. storing all data on a recording medium.

32. An electrocardiograph system comprising:
 a. means for sensing an electrocardiograph signal, the signal comprising a successin of waves;
 b. independently identifying the QRS complex with each successive wave continuously, in real-time, and in a beat-by-beat manner;
 c. means for independently analyzing data from the succession of QRS complexes relating to the cardiac function continuously, in real-time, and in a beat-by-beat manner, the means for analyzing is comprised of means for band-pass filtering the data in a high frequency range between about 150 Hz and about 250 Hz; and
 d. means for recording all data.

33. A method of monitoring cardiac function, comprising the steps of:
 a. sensing an electrocardiograph signal, the signal comprising a succession of waves;
 b. independently identifying the QRS complex with each successive wave continuously, in real-time, and in a beat-by-beat manner;
 c. independently analyzing data from the succession of QRS complexes, wherein the step of analyzing is comprised of band-pass filtering the data in a high frequency range between about 150 Hz and about 250 Hz, and evaluating the filtered data for the presence or absence of a reduced amplitude zones continuously, in real-time, and in a beat-by-beat manner; and
 d. recording all data on a recording medium.

34. An electrocardiograph system comprising:
 a. means for sensing an electrocardiograph signal, the signal comprising a succession of waves;
 b. means for independently identifying the QRS complex with each successive wave continuously, in real-time, and in a beat-by-beat manner;
 c. means for independently analyzing data from the succession of QRS complexes relating to the cardiac function, wherein the step of analyzing is comprised of band-pass filtering the data in a high frequency range between about 150 Hz and about 250 Hz, and evaluating the filtered data for the presence or absence of reduced amplitude zones continuously, in real-time and in a beat-by-beat manner; and
 d. means for recording all data.

* * * * *